(12) United States Patent
Cooper

(10) Patent No.: US 7,192,424 B2
(45) Date of Patent: Mar. 20, 2007

(54) DISPOSABLE URINARY COLLECTION DEVICE HAVING ELASTIC PENIS OPENING ORTHOGONAL TO ELASTIC HAND OPENING

(76) Inventor: Teresa Cooper, 662 Golden Eagle Way, Lancaster, PA (US) 17601

( * ) Notice: Subject to any disclaimer, the term of this patent is extended or adjusted under 35 U.S.C. 154(b) by 261 days.

(21) Appl. No.: 11/074,332

(22) Filed: Mar. 7, 2005

(65) Prior Publication Data

US 2006/0200102 A1 Sep. 7, 2006

(51) Int. Cl.
*A61M 29/00* (2006.01)
*A61F 13/00* (2006.01)

(52) U.S. Cl. .................. 604/544; 604/385.09; 4/144.2; 24/122

(58) Field of Classification Search ........ 604/346–347, 604/349–353, 355–356, 385.09, 544, 327; 128/885; 4/144.2, 144.3; D24/122–123; 119/850
See application file for complete search history.

(56) References Cited

U.S. PATENT DOCUMENTS

| | | | |
|---|---|---|---|
| 2,439,683 A | 4/1948 | Broderick | 128/295 |
| 3,211,132 A * | 10/1965 | Hersh | 604/385.09 |
| 3,613,123 A | 10/1971 | Langstrom | 4/119 |
| 4,553,967 A | 11/1985 | Ferguson et al. | 604/317 |
| 4,601,716 A | 7/1986 | Smith | 604/349 |
| 4,779,573 A * | 10/1988 | Vidal | 119/868 |
| 4,790,834 A | 12/1988 | Austin | 604/349 |
| 4,886,509 A | 12/1989 | Mattsson | 604/349 |
| 5,695,485 A | 12/1997 | Duperret et al. | 604/349 |
| 6,324,704 B1 * | 12/2001 | Imo | 4/144.2 |
| 6,406,462 B1 | 6/2002 | Johnson | 604/327 |
| 6,530,909 B1 | 3/2003 | Nozaki et al. | 604/349 |
| 6,540,729 B1 | 4/2003 | Wada et al. | 604/349 |
| 6,569,135 B1 | 5/2003 | Mula | 604/349 |
| 6,635,038 B2 | 10/2003 | Scovel | 604/353 |
| D489,149 S * | 4/2004 | Horner | D29/113 |
| 2003/0028161 A1 | 2/2003 | Carballo | 604/349 |

* cited by examiner

*Primary Examiner*—Tatyana Zalukaeva
*Assistant Examiner*—Laura C. Hill
(74) *Attorney, Agent, or Firm*—Andrew D. Mead

(57) ABSTRACT

A less invasive disposable urinary collection device for receiving a penis of a male patient comprises a freestanding bulb-shaped sack formed from a single sheet of laminate material. The sheet includes a first absorbent inner layer disposed between a moisture impervious outer layer and a second absorbent layer. The sack has a top hand insertion opening with elastic and an elastic passageway disposed orthogonal to the hand opening for securing the sack to the penis.

3 Claims, 2 Drawing Sheets

DISPOSABLE URINARY COLLECTION DEVICE HAVING ELASTIC PENIS OPENING ORTHOGONAL TO ELASTIC HAND OPENING

FIELD OF THE INVENTION

The invention relates to a disposable urinary collection device and, more particularly, to a disposable urinary collection device for males that is a substitute for a catheter.

BACKGROUND OF THE INVENTION

It is often necessary to connect a bedridden or substantially immobile patient to a catheter in order collect the patient's waste. One example of a conventional catheter includes a heavy-gauge latex rubber condom that is attached to a receptacle through a tube. The condom is closely fitted to the patient's penis where it remains attached for an extended period of time. Because the condom in not readily flexible, the condom restricts circulation and causes swelling of the patient's penis. Additionally, perspiration and other bodily secretions accumulate between the patient's penis and the surrounding condom after an extended period of wear, which can cause infection and/or excoriation of the penis. It is therefore desirable to develop a disposable urinary collection device that is less evasive than the conventional catheter and eliminates side effects, such as infection and/or excoriation associated with the conventional catheter.

SUMMARY OF THE INVENTION

The invention is a disposable urinary collection device for receiving a penis of a male patient comprising a bulb-shaped sac formed from a single sheet of material. The sheet has edges drawn together by a first elastic member to form a gathered hand insertion opening. The bulb-shaped sac has a passageway extending through a side thereof for receiving the penis. An outer perimeter of the passageway has a second elastic member for securing the sac to the penis.

The invention further is a disposable urinary collection device for receiving a penis of a male patient comprising a bulb-shaped sac formed from a single sheet of material. The sheet has edges drawn together to form a gathered hand insertion opening. The bulb-shaped sac has a passageway extending through a side thereof for receiving the penis.

The invention still further is a disposable urinary collection device for receiving a penis of a male patient comprising a bulb-shaped sac having a gathered hand insertion opening. The bulb-shaped sac has a passageway extending through a side thereof for receiving the penis. The passageway is positioned approximately orthogonal to the gathered hand insertion opening.

DETAILED DESCRIPTION OF THE INVENTION

Figure 1:
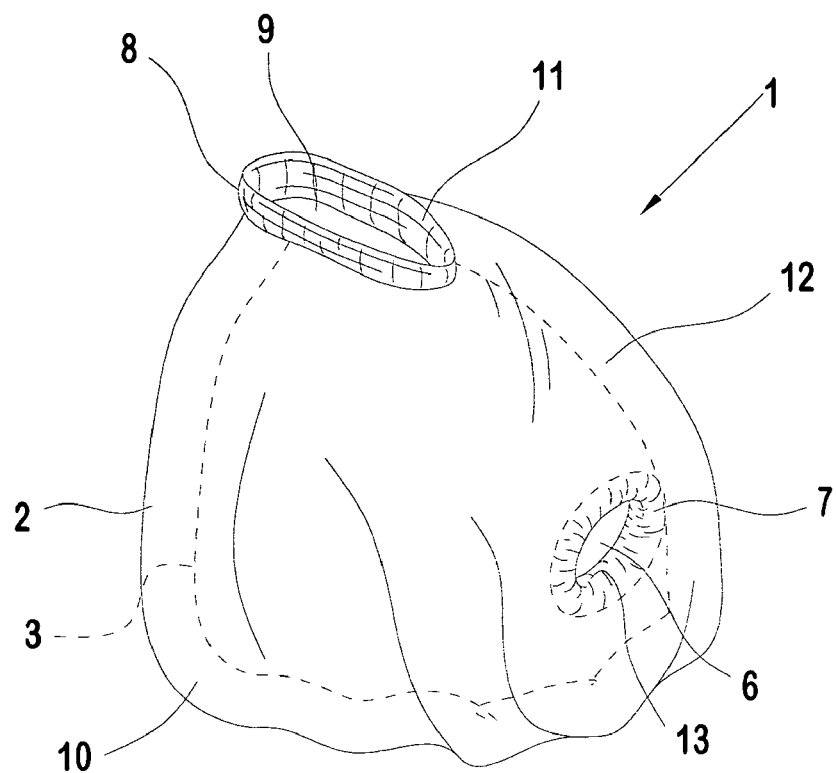
FIG. 1 is a perspective view of a disposable urinary collection device.
Figure 2:
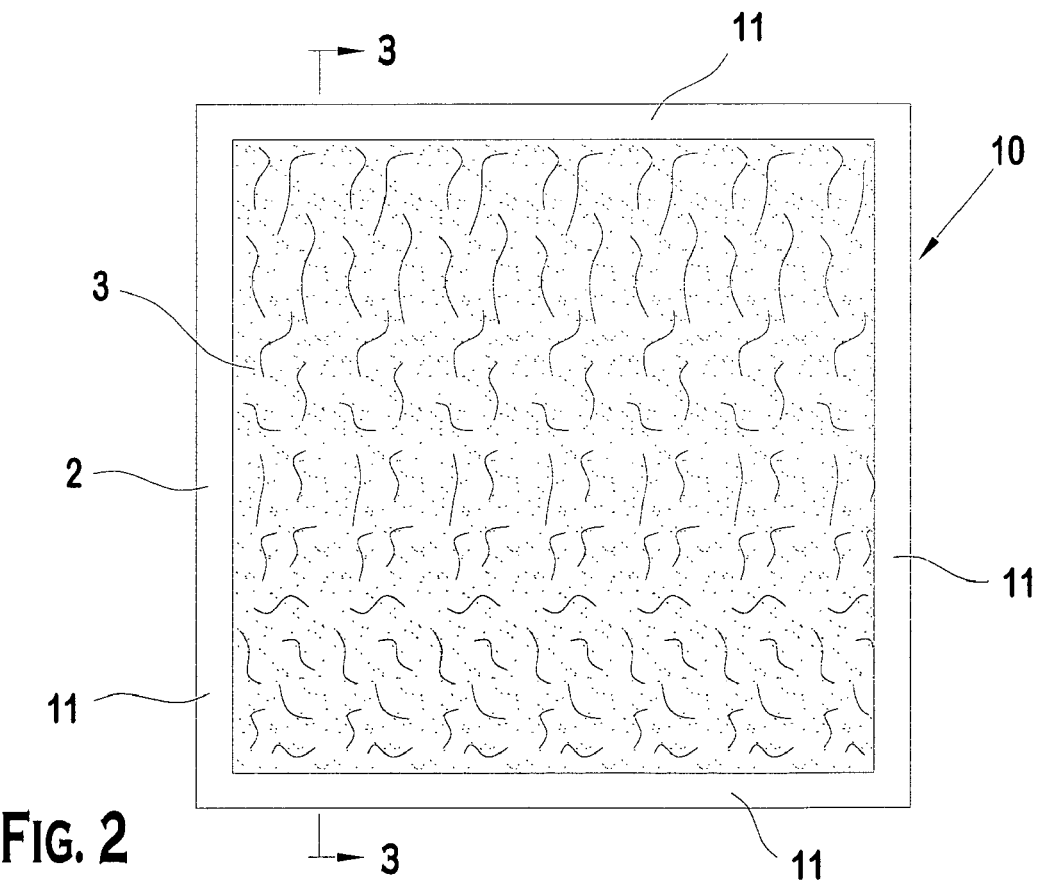
FIG. 2 is plan view of a flat sheet used to fabricate the disposable urinary collection device shown in FIG. 1.
Figure 3:
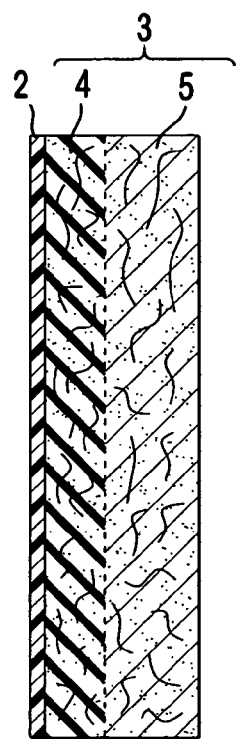
FIG. 3 is a cross-sectional view of the flat sheet taken along line 3–3 of FIG. 2.

FIG. 1 shows a disposable urinary collection device 1. The disposable urinary collection device 1 is formed from a single sheet 10 that includes an outer layer 2 and an inner layer 3, as shown in FIG. 2. The outer layer 2 is formed from a moisture impermeable or liquid resistant material. For example, the material may be a polypropylene film or other commonly known material, such as the material provided on an outer surface of a disposable diaper or pad. As shown in FIG. 3, the inner layer 3 consists of a first inner layer 4 and a second inner layer 5. The first inner layer 4 is arranged between the outer layer 2 and the second inner layer 5 and is formed from a liquid absorbent material. For example, the material may be an absorbent polymer or other commonly known material, such as the intermediary material provided in a disposable diaper or pad. The second inner layer 5 is formed from a liquid absorbent material. For example, the material may be a fluff material, such as the material provided on an inner surface of a disposable diaper or pad. The outer layer 2, the first inner layer 4, and the second inner layer 5 may be sewn or otherwise fastened together, for example, with an adhesive, to prevent movement of the outer layer 2, the first inner layer 4, and the second inner layer 5 with respect to each other.

As shown in FIGS. 1–2, edges 11 of the sheet 10 are gathered to form a sac 12 having a bulb-like shape and a gathered hand insertion opening 9. The edges 11 forming the gathered hand insertion opening 9 may be drawn together with a first cord or elastic member 8 so that the gathered hand insertion opening 9 is capable of stretching when a caretaker's hand (not shown) is inserted therethrough, to be described later. The sheet 10 is gathered such that the inner layer 3 faces toward an inside of the sac 12, and the outer layer 2 faces toward an outside of the sac 12. A passageway 6 is formed in a side of the sac 12. The passageway 6 is arranged approximately perpendicular to the gathered hand insertion opening 9. The passageway 6 may be formed before or after the edges 11 of the sheet 10 have been gathered. An outer perimeter 13 of the passageway 6 may be provided with a second cord or elastic member 7 so that the passageway 6 is capable of stretching when a patient's penis 15 is inserted therethrough, to be described later.

Figure 4:
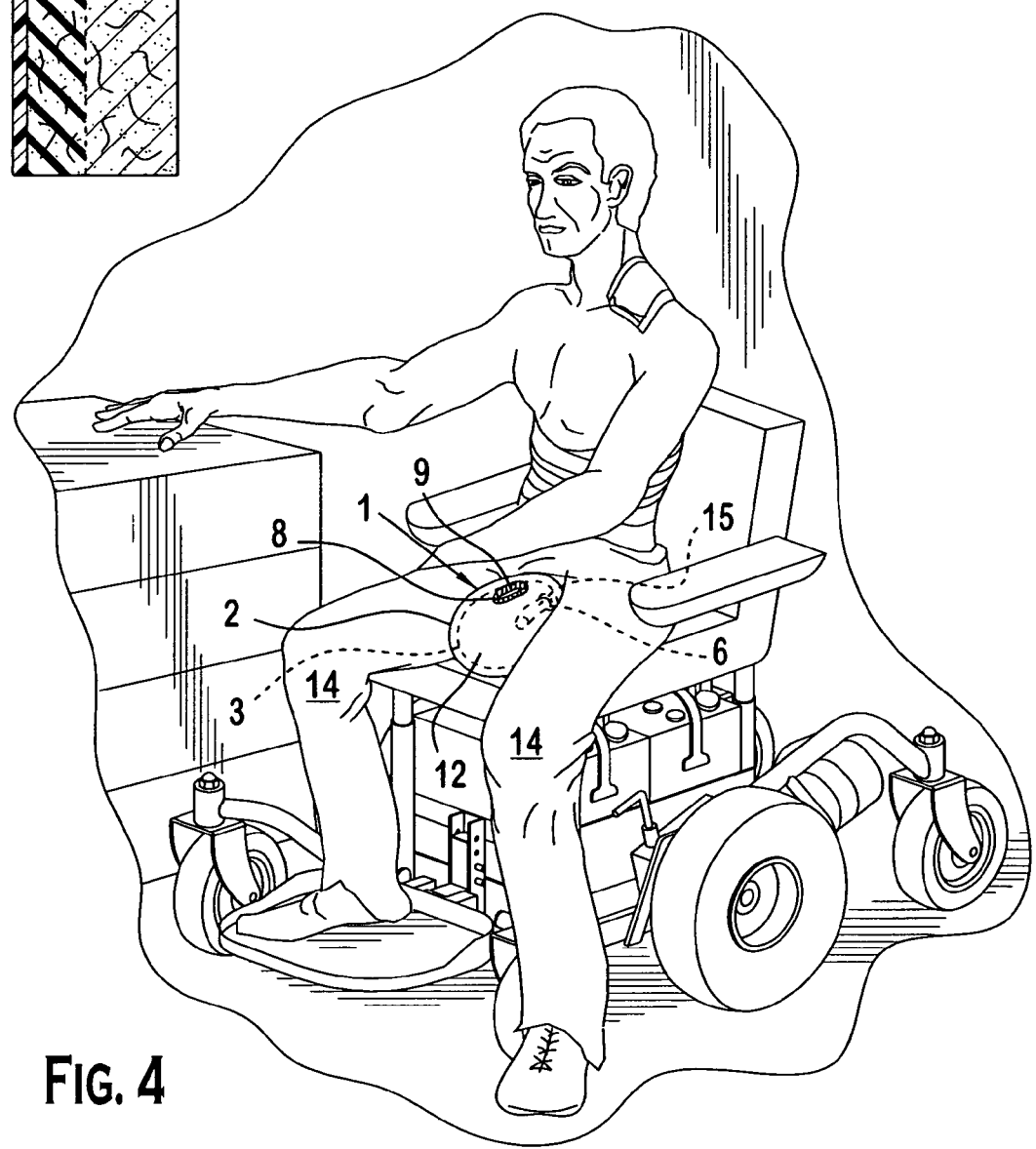
FIG. 4 is a schematic illustration of the disposable urinary collection device in use.

As shown in FIG. 4, in use, the caretaker (not shown) positions the disposable urinary collection device 1 between the patient's legs 14 with the gathered hand insertion opening 9 facing up and the passageway 6 facing the patient's penis 15. Because the sac 12 has a bulb-like shape, the urinary collection device 1 is capable of freestanding between the patient's legs 14. The patient may be either sitting, as shown in the illustrated example, or lying down. The caretaker (not shown) inserts their hand (not shown) through the gathered hand insertion opening 9. As the caretaker (not shown) inserts their hand (not shown) through the gathered hand insertion opening 9, the first elastic member 8 causes the gathered hand insertion opening 9 to stretch to facilitate insertion of the caretaker's hand (not shown) therein. The patient's penis 15 is inserted into the passageway 6 from an outside of the sac 12, as the caretaker (not shown) gently pulls the patient's penis 15 through the passageway 6 and into the sac 12 with their hand (not shown). As the patient's penis 15 advances through the passageway 6, the second elastic member 7 causes the passageway 6 to stretch to facilitate insertion of the patient's penis 15 therein. When insertion of the patient's penis 15 is complete, the second elastic member 7 serves to secure the sac 12 around the patient's penis 15. Once the patient's penis 15 is inside the interior of the sac 12, the caretaker removes their hand from the sac 12 through the gathered hand insertion opening 9.

The patient is then free to urinate in the sac 12. The urine, in addition to any other bodily secretions from the patient's penis 15, will be absorbed by the inner layer 3 and will be prevented from exiting the sac 12 by the outer layer 2. Moreover, the second inner layer 5 serves to wick the urination toward the first inner layer 4 so that the patient's penis 15 remains substantially dry before the disposable urinary collection device 1 is changed. After the sac 12 has been soiled, the caretaker (not shown) removes the sac 12 from the patient's penis 15 by simply pulling the sac 12 away from the patient's penis 15 until the patient's penis 15 is removed from the passageway 6. The disposable urinary collection device 1 is then deposited in a receptacle, and a new disposable urinary collection device 1 is positioned on the patient's penis 15. The disposable urinary collection device 1 is therefore a less evasive and healthier method of collecting urine from a patient than a conventional catheter.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A disposable urinary collection device for receiving a penis of a male patient, comprising:
   a bulb-shaped sack formed from a single sheet of laminate material and capable of standing freely between legs of the patient;
   said laminate material includes a first absorbent inner layer disposed between a moisture impervious outer layer and a second absorbent wicking inner layer;
   said laminate sheet comprises an opening sized to fit around a hand and located in the top of said sack, wherein said hand insertion opening has a first elastic member circumferentially disposed around the opening outer periphery;
   said sack additionally comprises a passageway sized to fit around a penis that is formed inside said laminate material and is positioned approximately orthogonal to the hand insertion opening on one side of the sack, wherein said passageway has a second elastic member circumferentially disposed around the opening outer periphery for securing said sack to the penis.

2. The device of claim 1, wherein said second inner layer is fluff.

3. The device of claim 2, wherein said first inner layer is an absorbent polymer.

* * * * *